US005769857A

United States Patent [19]

Reztzov et al.

[11] Patent Number: 5,769,857
[45] Date of Patent: Jun. 23, 1998

[54] LIGATING CLIP APPLIER

[75] Inventors: Alexander Vladimirovich Reztzov; Evgeniy Alekseevich Karpov, both of Moscow, Russian Federation

[73] Assignee: MGF Group Inc., San Francisco, Calif.

[21] Appl. No.: 661,499

[22] Filed: Jun. 11, 1996

[51] Int. Cl.⁶ ..................................................... A61B 17/00
[52] U.S. Cl. .......................... 606/143; 606/139; 606/151
[58] Field of Search .................................... 606/143, 142, 606/139, 151, 157, 158; 227/901, 902

[56] References Cited

U.S. PATENT DOCUMENTS

| | | | |
|---|---|---|---|
| 3,683,927 | 8/1972 | Noiles | 606/143 |
| 4,246,903 | 1/1981 | Larkin | 606/143 |
| 4,562,839 | 1/1986 | Blake, III et al. | 606/143 |
| 4,712,549 | 12/1987 | Peters et al. | 606/143 |
| 5,100,420 | 3/1992 | Green et al. | 606/143 |
| 5,282,807 | 2/1994 | Knoepfler | 606/143 |
| 5,300,081 | 4/1994 | Young et al. | 606/143 |
| 5,342,373 | 8/1994 | Stefanchik et al. | 606/142 |

Primary Examiner—Jeffrey A. Schmidt
Attorney, Agent, or Firm—Neal O. Willmann

[57] ABSTRACT

This document discloses a ligating clip applier which initially closes and locks a pair of complementary jaws around tissue to be ligated allowing the isolation of tissue for inspection, with the option to reposition, to ensure appropriate ligation. Upon further activation, a U-shaped clip having a flat crown perpendicular to a pair of parallel legs with rounded ends is advanced into the locked jaws of the instrument and converged around the isolated tissue until ligation is completed.

8 Claims, 13 Drawing Sheets

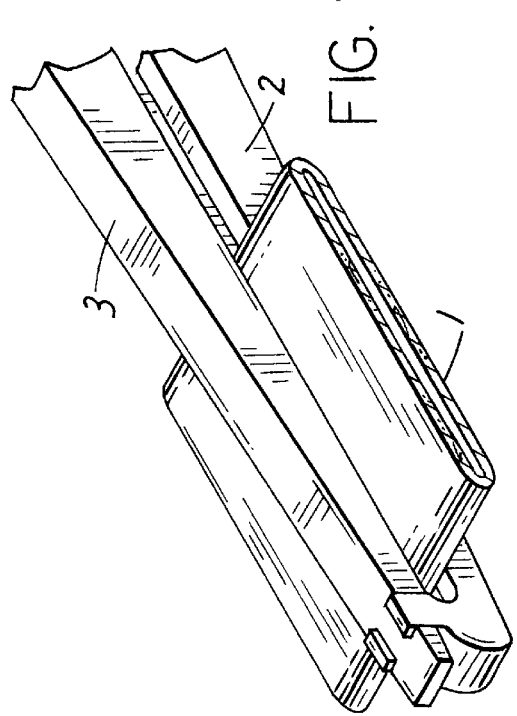
FIG. 2
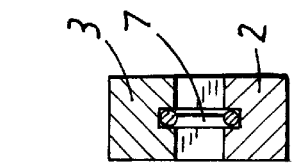
FIG. 4A
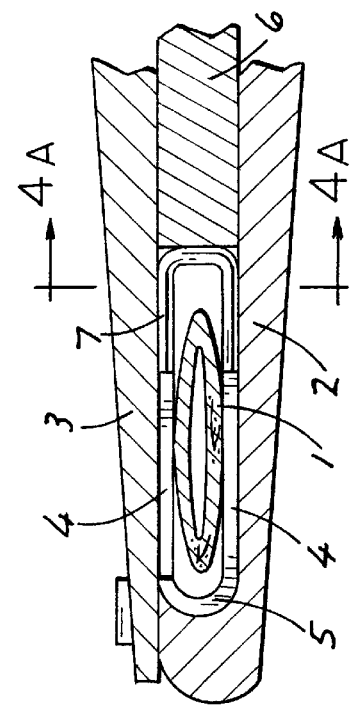
FIG. 4
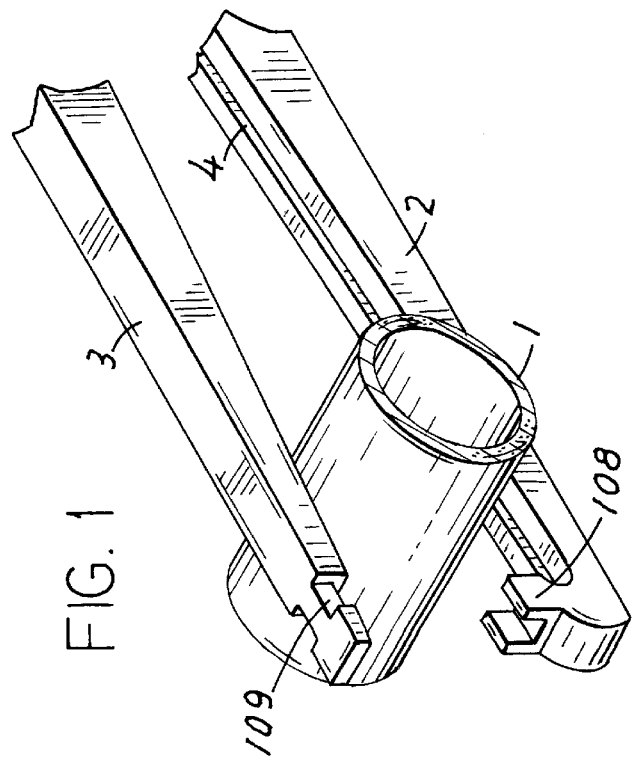
FIG. 1
FIG. 3

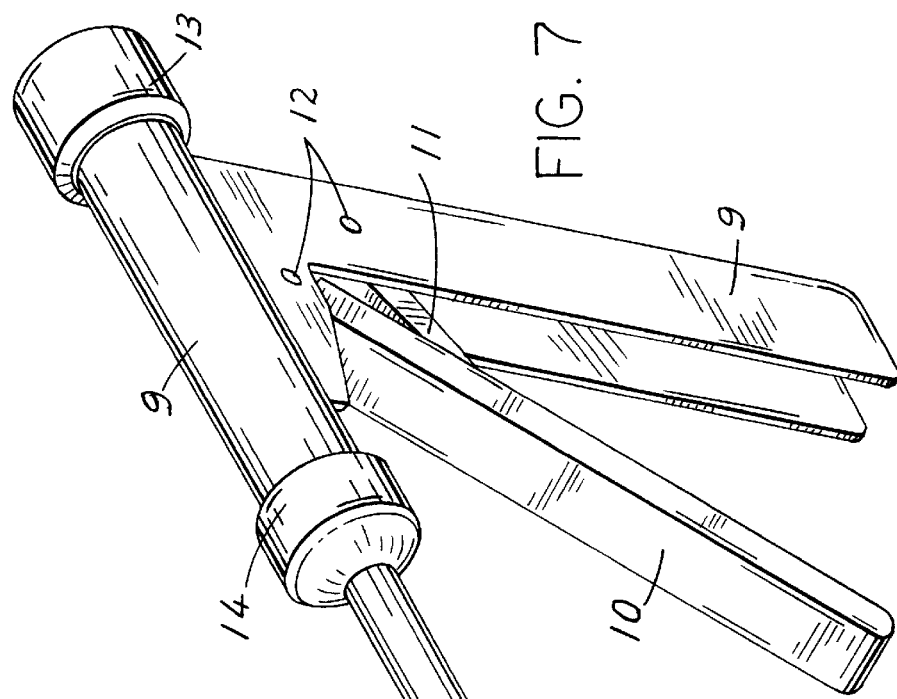
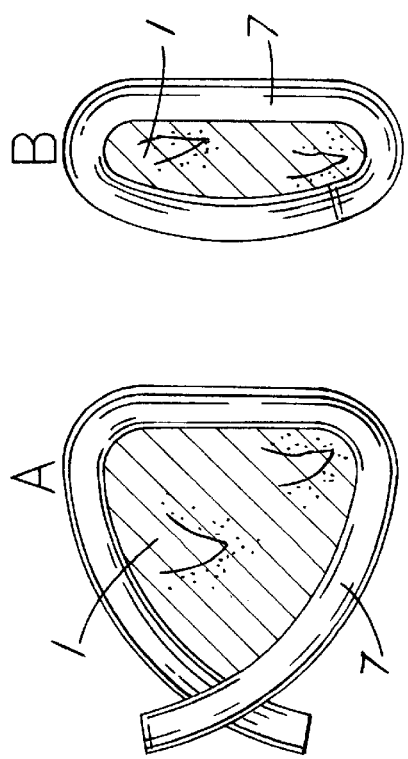
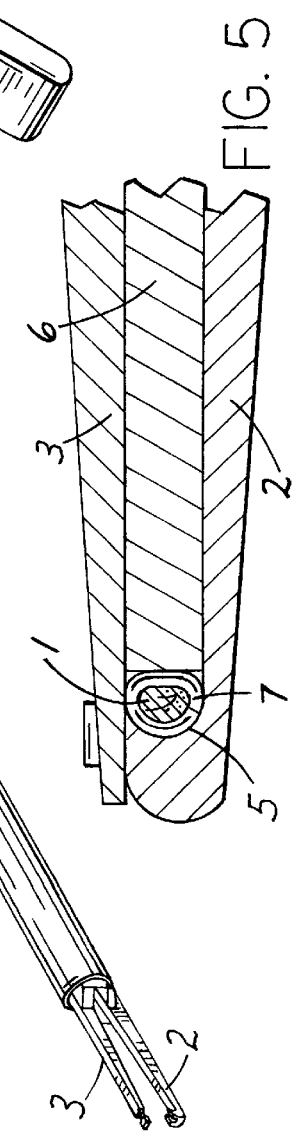
FIG. 7
FIG. 5
FIG. 6

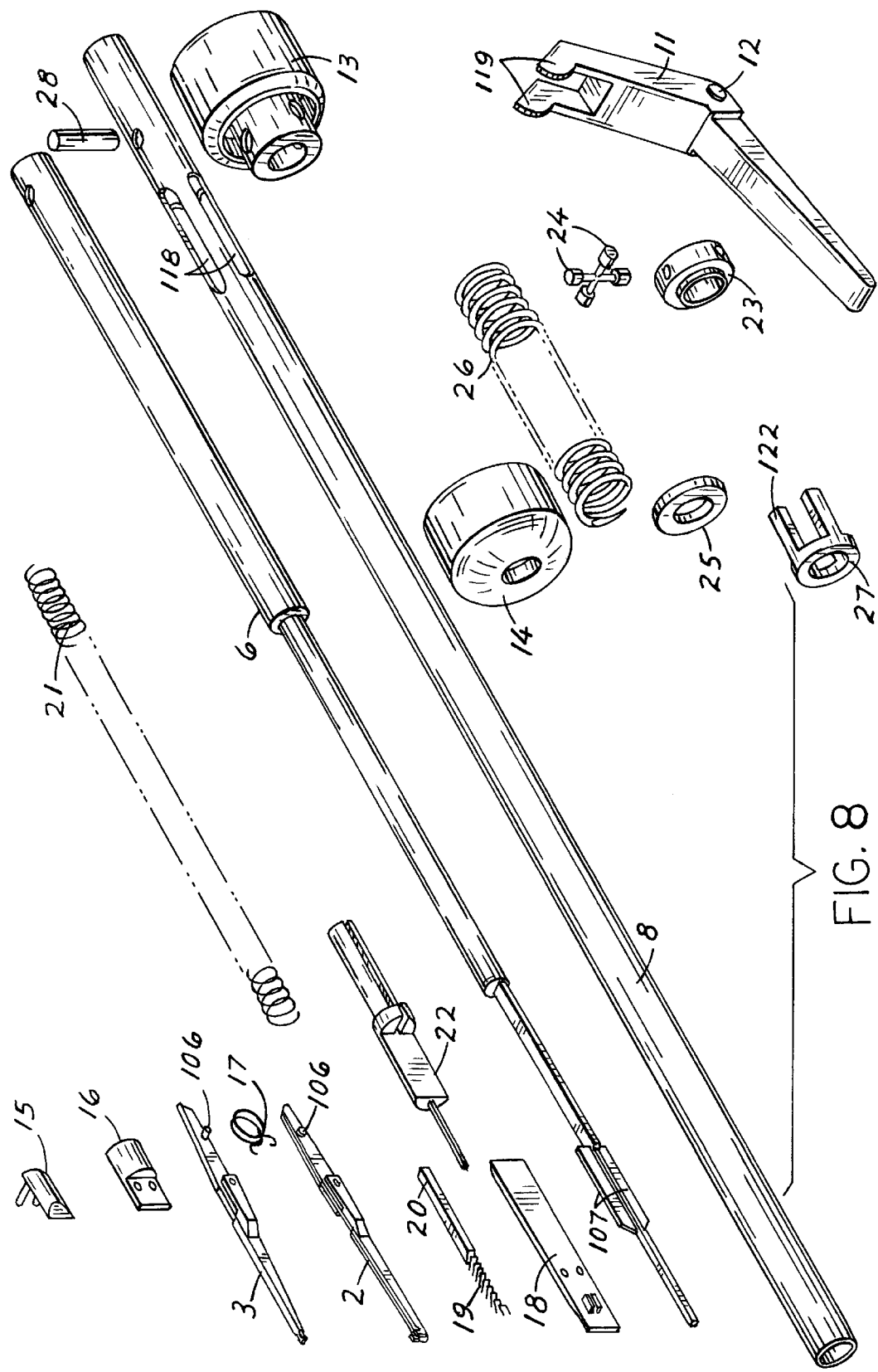

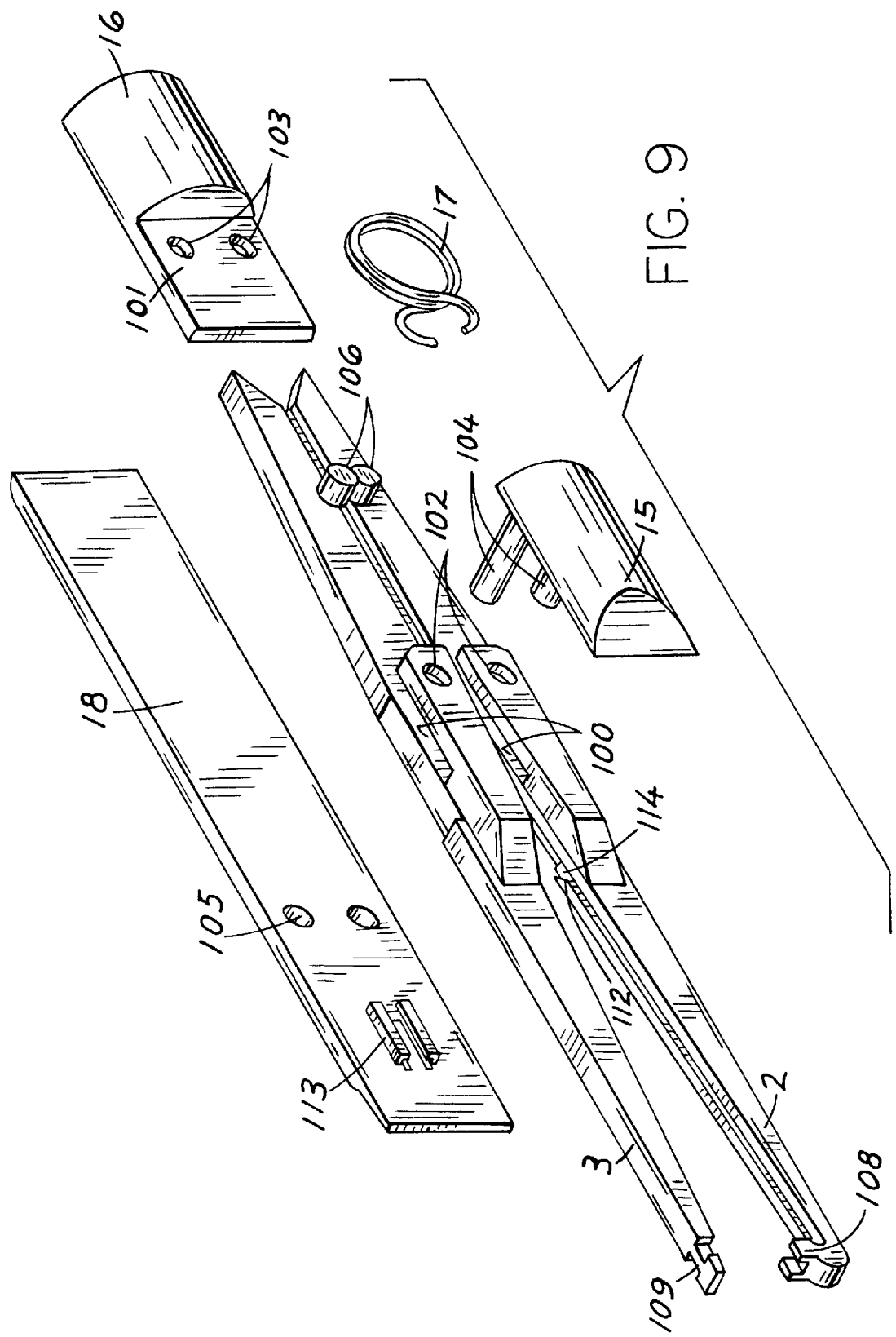

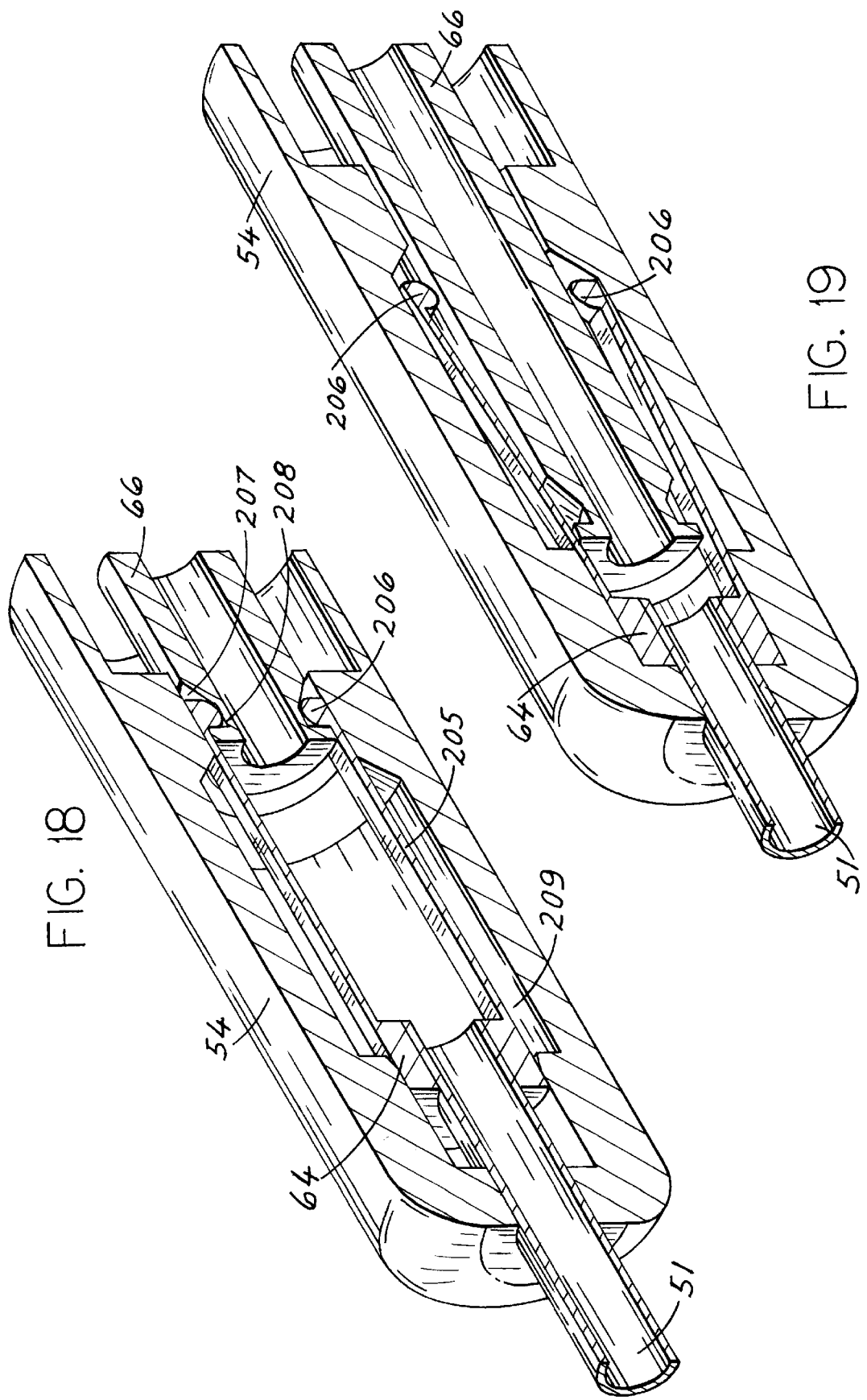

LIGATING CLIP APPLIER

BACKGROUND OF THE INVENTION

This disclosure relates generally to the field of surgical instruments and in particular to those instruments that are designed to occlude tissue, primarily hollow organs such as blood vessels and ducts, via ligation. More specifically, the disclosed instrument has been designed to meet the most demanding requirements of laparoscopic surgery with features a sealing system to prevent the seepage of insufflated gas from body cavities. The interlocking jaws of the disclosed instrument initially isolate the tissue to be occluded, offering the option of opening and closing numerous times; and, with sequential activation, effect ligation at precisely the desired location with virtually no chance of damage to the surrounding tissues and minimal trauma to the ligated tissue.

DESCRIPTION OF THE PRIOR ART

Relevant patent references to the device disclosed herein include U.S. Pat. No. 4,101,063 to Kapitanov et al. which discloses a surgical instrument for ligating tubular organs in deep body cavities, which when utilized in a manner most relevant to the instrument disclosed herein, has a needle-shaped die for grasping the hollow organ to be ligated and a spring-loaded fork mechanism for pressing the hollow organ against the needle-shaped die to effect ligation.

U.S. Pat. No. 5,431,668 to Burbank et al. describes a ligating clip applier with a jaw closure mechanism that allows the jaws to contact the legs of the ligating clip sequentially: first distally and then proximally to close the clip in said order to ensure that the angle of the clip legs at the crown is eliminated.

U.S. Pat. No. 5,431,669 to Thompson et al. discloses a surgical clip applying device having a hook for engaging and retaining, under tension, a tissue structure to be ligated while a clip advancing means moves a U-shaped clip into a pair of axially movable jaws and a jaw advancing means moves the jaws and clip so that the tissue structure is disposed between the jaws and ligated upon closure of said jaws.

U.S. Pat. No. 5,192,288 to Thompson et al. describes an apparatus with a shaft for applying surgical clips to normally inaccessible body tissue notably including a means for closing the clips by employing an anvil mounted at the distal end of the shaft and a hammer movable against the anvil.

SUMMARY OF THE INVENTION

The presently disclosed ligating device is distinguished from and improves upon the instruments in the prior art by providing a means for applying ligating clips which isolates the tissue to be ligated, providing an opportunity to inspect the tissue to be ligated and reposition the instrument, if needed, without damage to the tissue. The device comprises a handle assembly, including an activating mechanism; an elongated shaft connected to said actuating mechanism and extending distally from said handle and a pair of jaws responsive to sequential activation to close, then to interlock forming an enclosure for the isolation of tissue to be ligated and providing coordinated tracks for guiding activated clips into the distal end of said locked jaws where the distal ends of said clips are converged unopposed to ligate tissue with minimal damage.

This disclosure also describes various embodiments of the ligating clip applier, especially with regard to jaw closure and clip size adjustment. It is also the purpose of this disclosure to describe a metallic, surgical grade, biocompatable clip that is designed to ligate effectively a wide range of tissue thicknesses. The clips are formed from an extruded wire, generally having a circular cross section. This clip will essentially have a U-shape and a flat crown substantially perpendicular to the distally extending parallel legs which terminate in rounded or blunt ends.

BRIEF DESCRIPTION OF THE DRAWINGS

FIGS. 1 & 2 are perspective views of the upper and lower jaws in the open and closed positions.

FIG. 3 is a cross sectional view through the upper and lower tracks of the interlocking jaws.

FIG. 4 is the same as view of FIG. 3 with the clip driver and clip partially advanced.

FIG. 4a is a cross section of FIG. 4 taken along line A—A.

FIG. 5 is a cross sectional view of the interlocking jaws with the clip driver fully extended and the clip fully formed.

FIG. 6 presents side views of (a) clip showing a minimally closed configuration and (b) clip showing a maximally closed configuration.

FIG. 7 is a perspective view of the ligating device.

FIG. 8 is an exploded view of jaws, shaft, clip-size adjustment, shaft rotation mechanism and their components.

FIG. 9 is a schematic exploded view of the jaw assembly and clip cartridge.

FIG. 18 is a perspective view of the activating mechanism for transforming a single trigger motion into two simultaneous, controlled actions: one action for closing the jaws and the other for clip-size adjustment, said mechanism compatible with the device of FIG. 12. The depiction in FIG. 18 would have the jaws open and the clip driver retracted.

FIG. 19 is the same view as FIG. 18, but in this depiction, the jaws would be closed and the clip driver extended distally.

DESCRIPTION OF THE PREFERRED EMBODIMENTS

Figure 10:
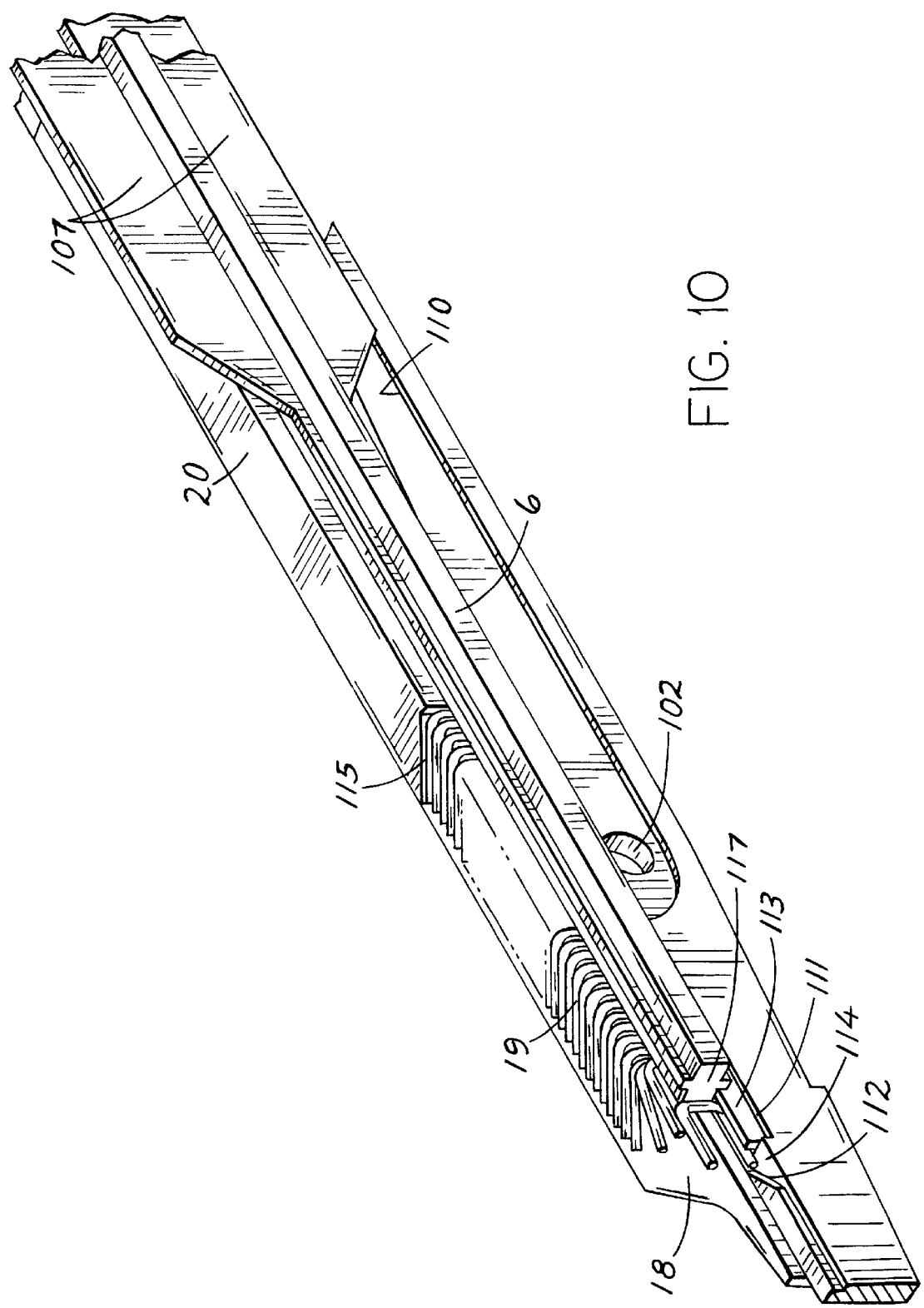
FIG. 10 is a perspective cross sectional view of the cartridge assembly.
Figure 11:
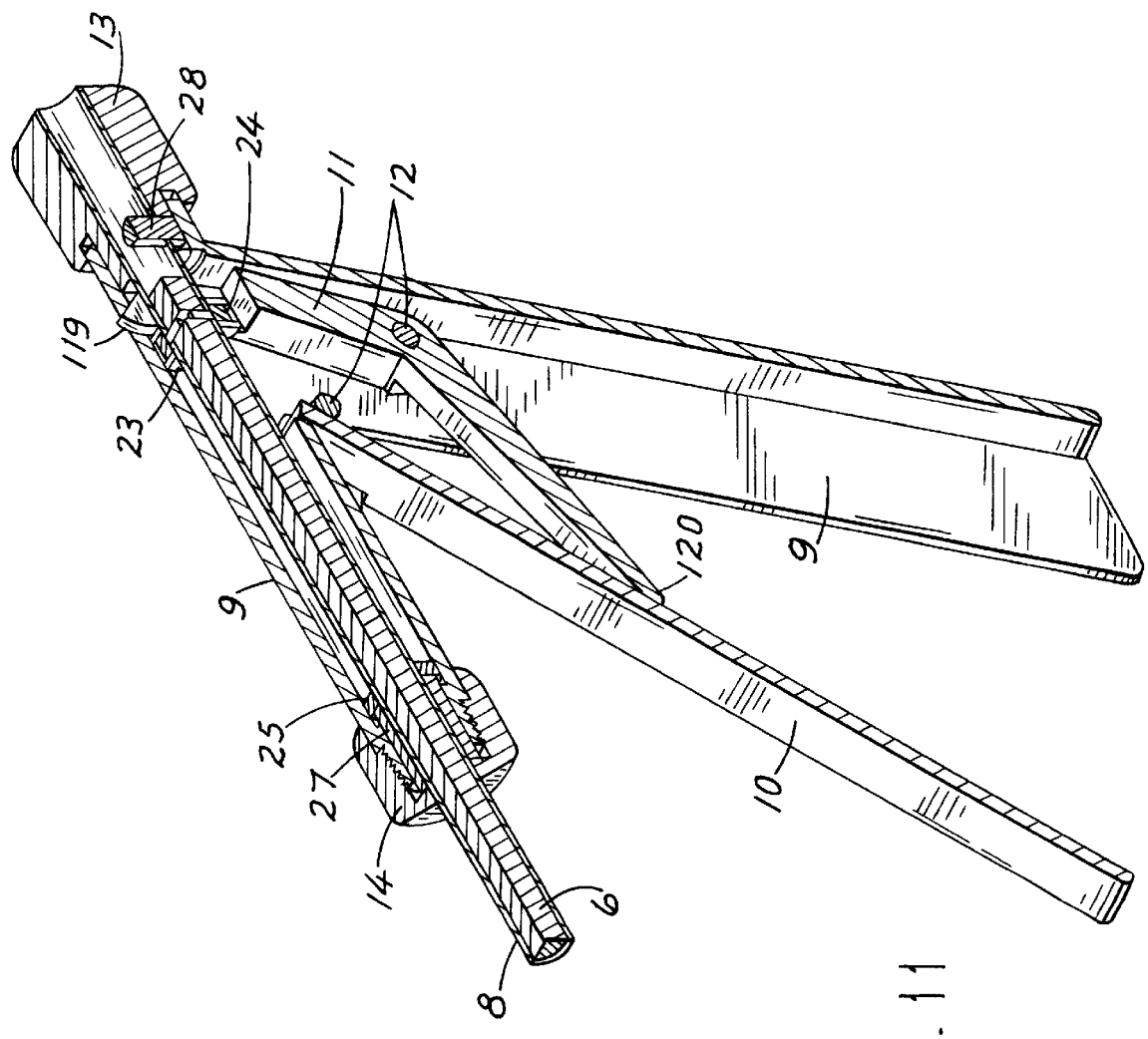
FIG. 11 is a perspective cross sectional view of the handle, clip-size adjustment and shaft rotation mechanisms.

In the most basic and general terms, the disclosed instrument ligates tissue in two steps: Tissue is secured within the jaws of the clip applier, and ligation occurs with an adjustable U-shaped clip formed within the inner surfaces of the jaws. In somewhat greater detail, the blunt-tipped legs of a metallic U-shaped clip are advanced by a driver and guided in grooves within the inner surfaces of the jaws surrounding the tissue without penetrating it. With continuing distally-directed pressure, the clip completely encircles the tissue and encounters the anvil surface of the lower jaw where the legs converge unopposed, forming a ligating clip.

The disclosed instrument performs these steps of isolating and ligating tissue with the interaction of three structural elements:

1. A handle assembly which includes an activating mechanism for jaw closure, clip feeding and formation, shaft rotation and clip size adjustment.
2. A shaft, containing a supply of U-shaped clips, which is rotatable and connected to:
   the handle assembly
   the jaw closing mechanism
   clip feeding and forming mechanisms
   a clip-size adjustment mechanism.
3. A pair of interlockable jaws which surround the tissue to be ligated and provide tracks for clip guiding and a clip forming anvil located, preferably, within the lower jaw.

The first step in the operation of the instrument is to isolate the tissue to be ligated by containing it within the interlocking upper and lower jaws. This permits the surgeon to visually inspect the tissue in the jaws and reposition the instrument as necessary to ensure proper placement of the clip. If a significant amount of repositioning is necessary at this point in the procedure, the jaws can be opened by simply releasing pressure on the trigger. The rotatable shaft is designed to facilitate better positioning of the jaws and observation of the tissue.

When the jaws are properly positioned, a clip can be advanced until the legs of the unformed clip surround the jaw-enclosed tissue and are bent by an anvil in the interlocking jaws. In preferred embodiments, the anvil will be located in the lower jaw and double tracked to accommodate the converging clip leg from the upper jaw. The size of the formed clip can be adjusted by an adjusting mechanism, not through continued, uncontrolled trigger-initiated force on the clip.

For a better understanding and appreciation of the disclosed instrument, reference should be made to the drawings. Referring to FIGS. 1 and 3, a hollow organ 1 to be ligated is positioned between jaws 2 & 3 of the instrument. With compression on the trigger 10, the jaws are closed around the organ and ultimately interlocked. It should be noted from FIGS. 3 & 4 that the enclosed tissue is only slightly compressed, and the device can be repositioned around the tissue without opening the jaws, or the jaws can be opened simply by releasing the trigger, without advancing or forming a clip, and re-positioned around the tissue without damaging the tissue. In FIGS. 3 & 4, it is apparent that the tissue has been positioned to be ligated. In FIG. 4, the clip driver 6 has been activated by further compression of the trigger, and has advanced an unformed clip 7 along tracks 4 recessed within the inner surface in both the upper and lower jaws. In FIG. 5, the driver has been fully activated and extended distally to the clip-forming surface identified as the anvil 5 in the distal end of the lower jaw so that the clip has been fully formed around the tissue and ligation is complete. Note that the blunt tipped U-shaped clip is designed to surround the tissue, not penetrate it. FIG. 6 illustrates schematically how clip-size formation can be adjusted to effect different degrees of closure using the same clip size. FIG. 6a shows a formed clip ligating a relatively large tissue cross-section and FIG. 6b shows the same sized clip ligating a smaller cross-section. The formed clip size is determined by the distance between the anvil 5 and the front surface of the clip driver 6 in its full-forward position. This distance is pre-set by the clip-size adjustment knob which will be described later.

FIG. 7 provides a perspective view of one embodiment of the disclosed instrument. Elements of the device that have not yet been fully described include the outer tube 8, which houses the shaft and its various actuating mechanisms, and the handle assembly 9 including other activating components such as the trigger 10 and the crank 11, as well as the shaft rotation knob 13 and the clip adjustment knob 14.

The trigger 10 and crank 11 are connected by pins 12 to the handle 9. The forked end 119 of the crank is designed to transmit force to the driver 6 through ring 23 which is held in place by screws 24. Spring 26, located between rings 25 and 23, is compressed on activation so as to decompress on relaxation of the trigger at the end of the firing sequence thereby opening the jaws and returning the driver to its initial position.

FIG. 8 presents an exploded view of the instrument showing all the parts necessary for a preferred embodiment of the clip applier to function as described.

A clip adjustment knob 14 is screwed into the distal end of handle 9. As mentioned, knob 14 controls clip size and tissue compression by transmitting a force through spacer 27 and ring 25 to shift the position of the outer tube 8 and jaws 2 & 3 relative to driver 6. The shaft rotation knob 13, positioned at the proximal end of handle 9, is connected to outer tube 8 by locking pin 28.

The clip cartridge 18, replaceable if desired, contains clips 19 and the clip stack driver 20. The cartridge can be permanently attached to the outer tube 8, if desired. When cartridge replacement is desired, it can be held in place with appropriate fastening means.

To initiate activation of the instrument, the trigger 10 is compressed and rotated around pin 12 to cause crank 11 to rotate as well. The fork 119 of crank 11 pushes ring 23 which moves driver 6 forward compressing return spring 26. Spring 21 is also compressed, forcing clip stack pusher 22 forward to keep tension on the clip stack. When driver 6 is advanced, the ribs 107 at the distal end of the driver 6 force apart the proximal ends of the jaws, thus closing the distal ends around the tissue to be ligated. To enable the distal ends of said jaws 2 and 3 to close, the proximal ends of said jaws pivot around pins 104 of anchor 15. Pins 104 first protrude through holes 102 of jaws 2 and 3 and then continue through holes 103 of anchor mate 16. Tongue 101 of anchor mate 16 enters pockets 100 of jaws 2 and 3, and aligns holes 103 with pins 104, which also protrude through holes 105 of element 18, thus creating a housing from elements 15, 16 and 18 within which jaws 2 and 3 pivot to enable distal closing of said jaws. In order to interlock and to ensure proper alignment of the jaws, this embodiment has protrusions 108 on lower jaw 2 which are designed to fit the cut-outs 109 in the upper jaw 3. The mating of the jaws provides the structural rigidity necessary to eliminate the possibility of jaw misalignment during clip formation. This rigidity also enables the use of small, thin, easily positioned jaws. As driver 6 retracts, its ribs 107 also retract allowing the jaw opening spring 17 on pins 106 to decompress, opening the jaws, releasing the tissue and returning the jaws to their initial position. Note that the jaws close at the start of the initial forward movement of the driver 6, prior to the release of a clip from cartridge 18. The ribs 107 in the driver hold the jaws closed for the duration of the driver's distal motion. Groove 110 is the track on which the driver ribs travel. When the jaws are closed, the recession 111 mates with the protrusion 113 of cartridge 18. This protruding part 113 of the cartridge holds the next clip to be activated. The tapered surface 112 guides the legs of the clip from the protruding part 113 into grooves 4 in the jaws.

Clip stack 19 and the clip stack driver 20 are situated within the cartridge 18. In this embodiment, the clips are positioned in an angled side-to-side configuration in order to facilitate ejection form the cartridge. The distal end 115 of the clip stack driver 20 is angled to permit the movement of the clip to be ejected from the cartridge and into the grooves 4 in the jaws and matches the angle of the clip stack 19. As the clip leaves the clip stack, edge 117 of the driver 6 advances a clip into protrusion 113 of the cartridge, provides for its distal movement, and prevents clip stack 19 from advancing another clip. At this point, driver 6 can advance the clip from protrusion 113 into the jaw grooves 4. Prior to clip activation, of course, the ribs 107 of the driver 6 have entered the proximal ends of the jaws 2 & 3, thus closing the distal ends.

While the driver 6 advances the clip to be formed toward the anvil 5, it prevents clips in the clip stack 19 from progressing farther, keeping them in position while the driver ribs 107 keep the jaws in a closed configuration. When the driver is in its full forward position, the clip is formed and the tissue ligated. In the return stroke, driver 6 retracts past the cartridge clip stack and releases the most distal clip in stack 19 which is advanced forward by clip stack driver 20. The driver ribs 107 retract, allowing the jaw opening spring 17 to decompress and open the jaws.

The shaft is easily rotatable during surgery. The shaft rotation knob 13, positioned at the proximal end of handle 9, can be rotated, which correspondingly, rotates outer tube 8 through locking pin 28. The rotating outer tube causes screws 24 to simultaneously rotate driver 6 and ring 23. In the same manner, both the driver 6 and the outer tube 8 turn all of the components within the tube including jaws 2 and 3.

Turning the clip size adjustment knob 14, which is threaded on the distal end of the handle body, transmits a force through spacer 27 and ring 25. The extensions 122 of spacer 27 enter the corresponding grooves in the body of the handle and advance ring 25 which is permanently attached to tube 8. The overall effect of turning the clip adjustment knob 14 is to move outer tube 8 and the jaws relative to the driver 6. The closer the anvil 5 in the interlocking jaws is to the driver 6, the smaller will be the final size of the formed clip.

Figure 12:
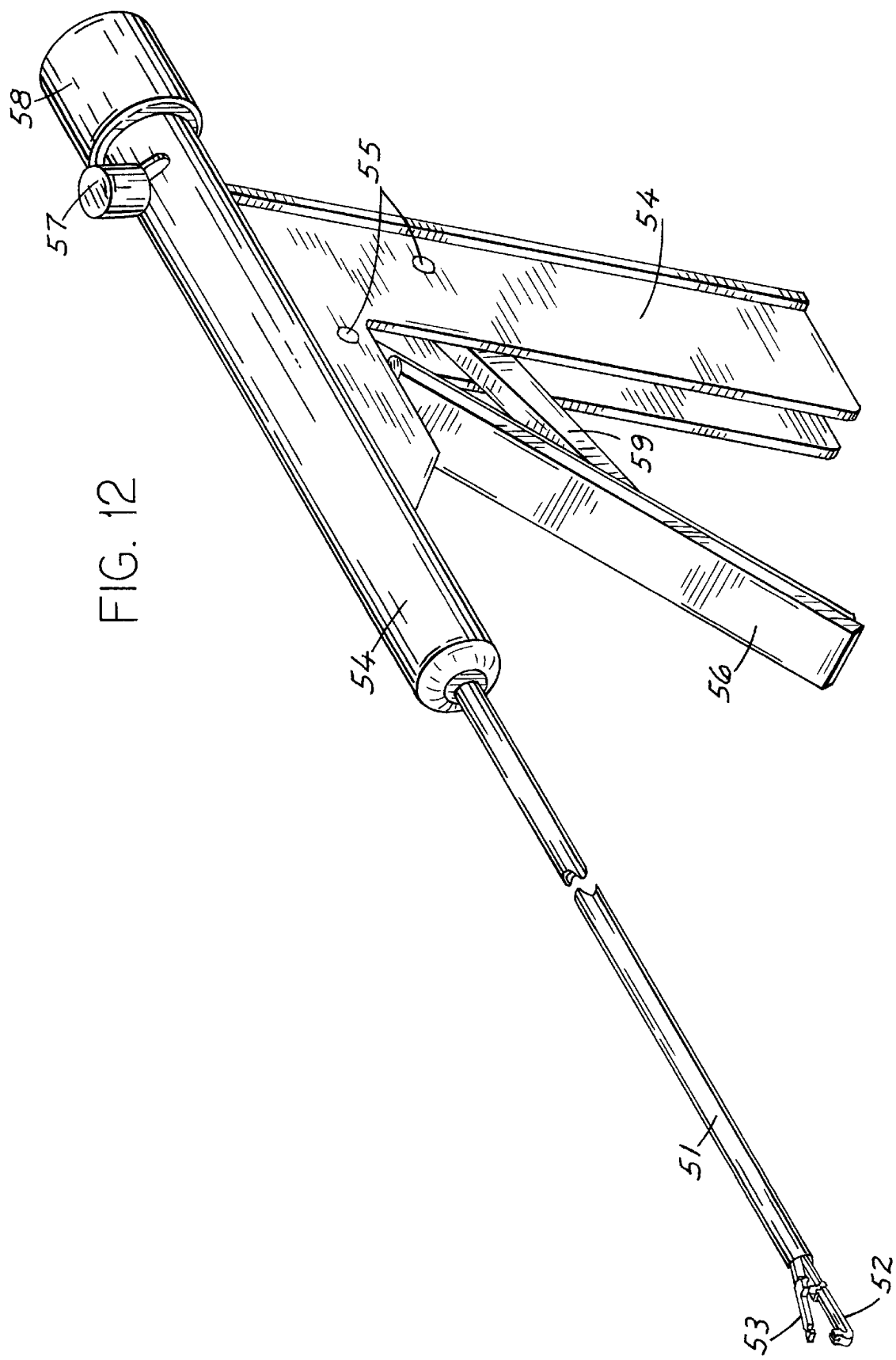
FIG. 12 is a perspective view of an alternative embodiment of the ligating device.
Figure 13:
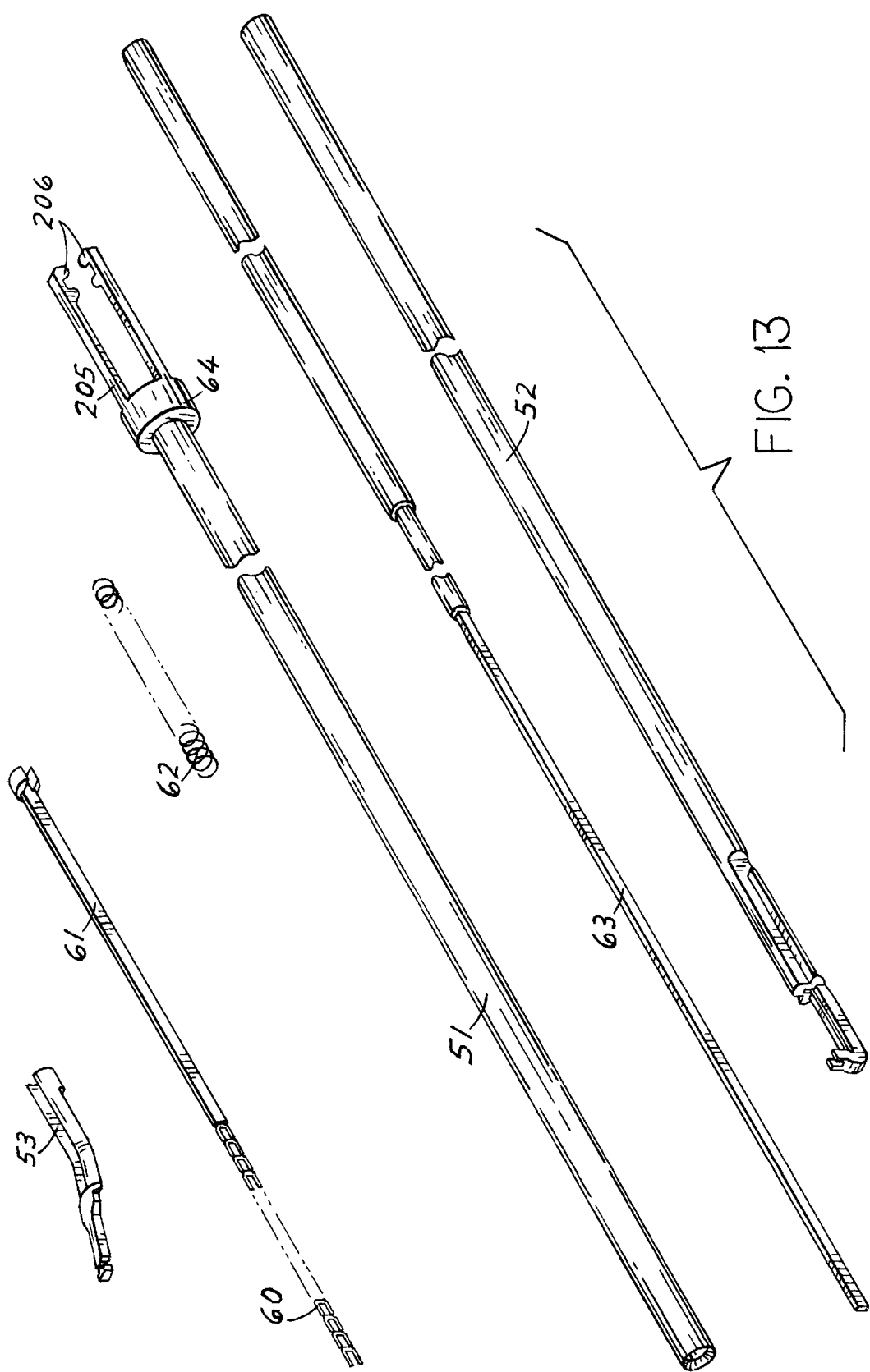
FIG. 13 is an exploded view of the jaw and shaft components for the device of FIG. 12.

Another embodiment of the disclosed device features different mechanisms for jaw closing and clip-size adjustment. Referring to FIG. 12, the rotating shaft of the device consists of jaw closure outer tube 51, lower jaw 52 and upper jaw 53. The shaft joins the stationary handle 54 which is connected to the trigger 56 and crank 59 through pins 55. The proximal end of the device contains the clip adjustment knob 57 and the shaft rotation knob 58.

The shaft for this embodiment of the device has a retaining spring 64 which is permanently affixed to the proximal end of the outer tube 51. The lower jaw 52 contains head-to-tail stacked clips 60, a clip stack driver 61 and a spring 62 for the clip stack driver.

Figure 14:
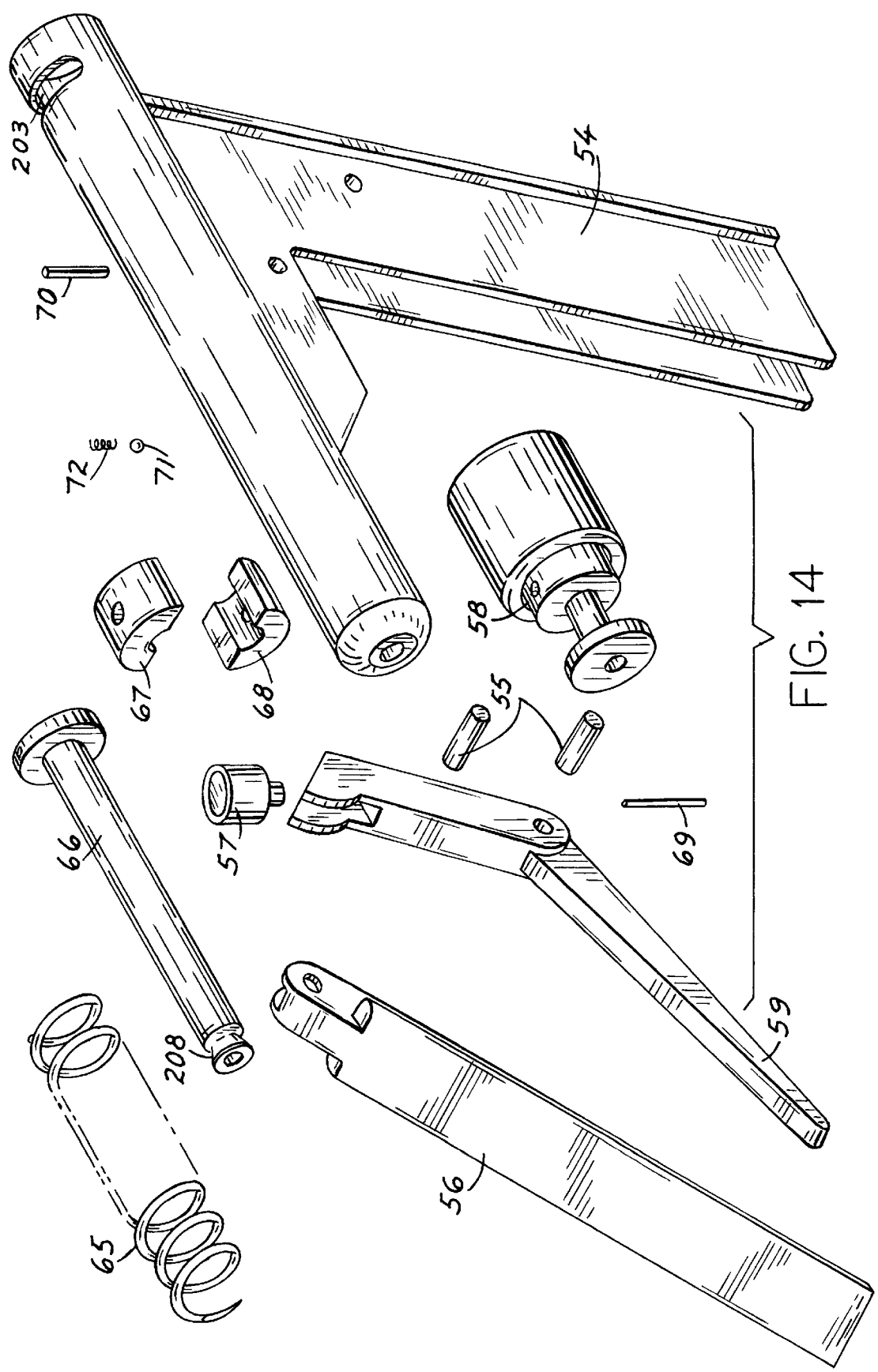
FIG. 14 is an exploded view of the handle, clip-size adjustment and shaft rotation components for the device of FIG. 12.
Figure 15:
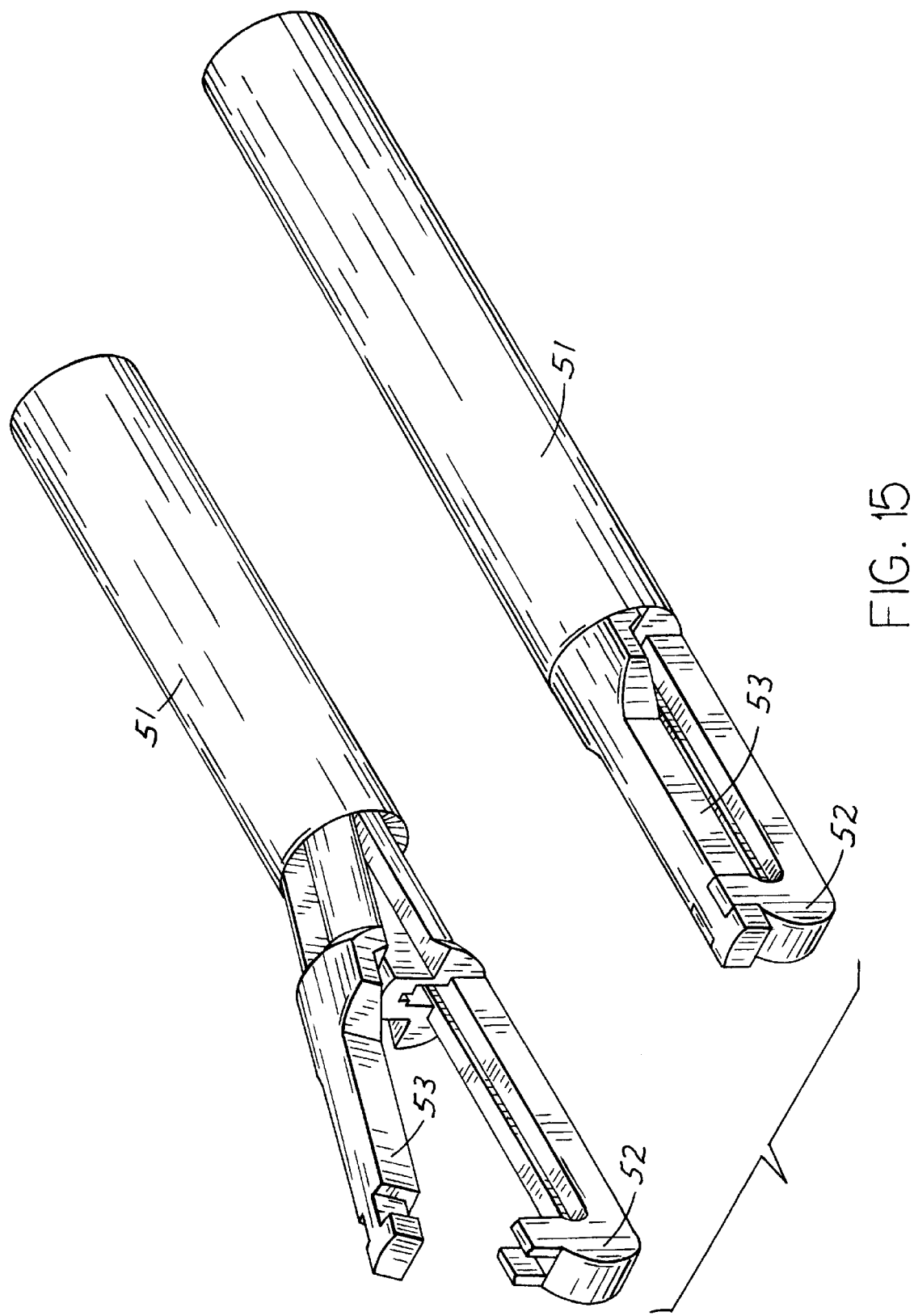
FIG. 15 is a perspective view of the open and closed jaws for the device of FIG. 12.

With reference to FIG. 14, the trigger 56, crank 59 and pins 55 are connected to the handle 54 in the same manner as in the other embodiment of the device. Spring 65 returns the jaws and driver to their initial positions at the end of the activation sequence. The forked end of crank 59, within the handle 54, activates connector 66 and advances it forward. The locking pin 69 joins connector 66 to clip forming driver 63.

The shaft rotation knob 58 is located at the proximal end of the handle 54. It interacts with and is connected to the lower jaws 52 with a locking pin 70. The upper and lower half-rings 67 and 68 are fitted in the groove in the handle to respond to the shaft rotation knob 58.

Figure 17:
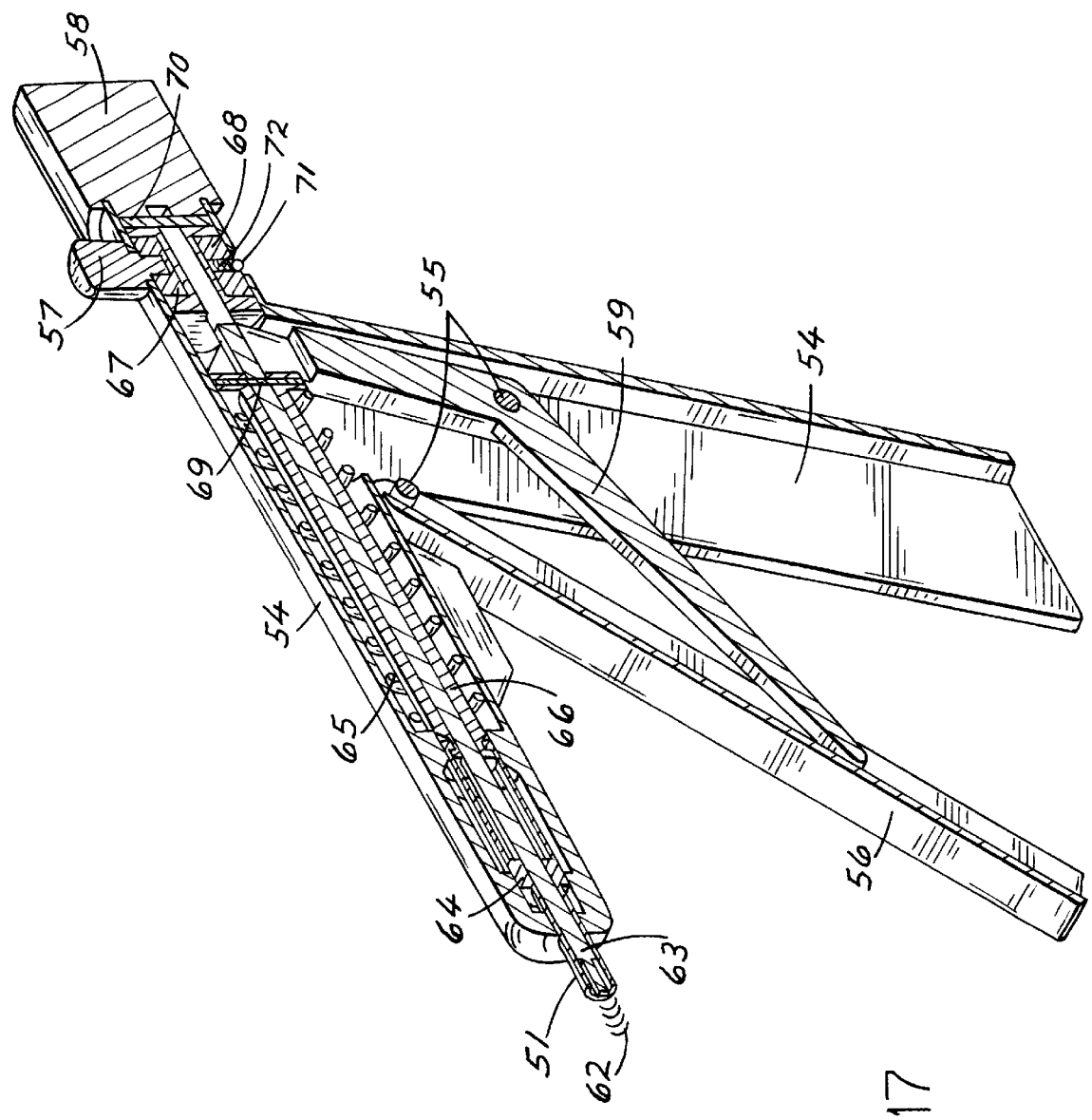
FIG. 17 is a perspective view in cross section of the handle, clip-size adjustment mechanism and shaft rotating mechanism for the device of FIG. 12.

Control of formed clip size and consequent vessel compression is achieved by moving lower jaw 52 with its anvil 5 relative to pusher 63. The upper and lower half-rings 67 & 68 are positioned in the groove of the shaft rotation knob 58 and the inner cylindrical surface of the handle 54. The clip size adjustment knob 57 is attached to the upper half-ring 67. It passes through the angled slot 203 in the handle 54. A ball 71 is located in the detente in lower half-ring 68. The ball is supported by retaining spring 72 and rests in the radial grooves 204 of the handle 54. In FIG. 17, the detent permits the use of discrete settings and reduces the likelihood of movement during clip formation.

Shifting knob 57 in the angled groove 203 causes movement of the jaw 52 relative to the handle. As a result, the distance between the lower jaw anvil 5 and pusher 63 changes, permitting the formation of different clip sizes when the device is activated.

Knob 58 is used by the surgeon to rotate the shaft of the instrument during surgery to re-orient the jaws without having to change the position of the handle.

Forward directed linear movement of the outer tube 51 over the upper and lower jaws causes them to close. The proximal end of upper jaw 53 acts as a spring, allowing the jaws to open when the outer tube 51 retracts. The jaw shanks mate together and require no additional fastening..

Figure 16:
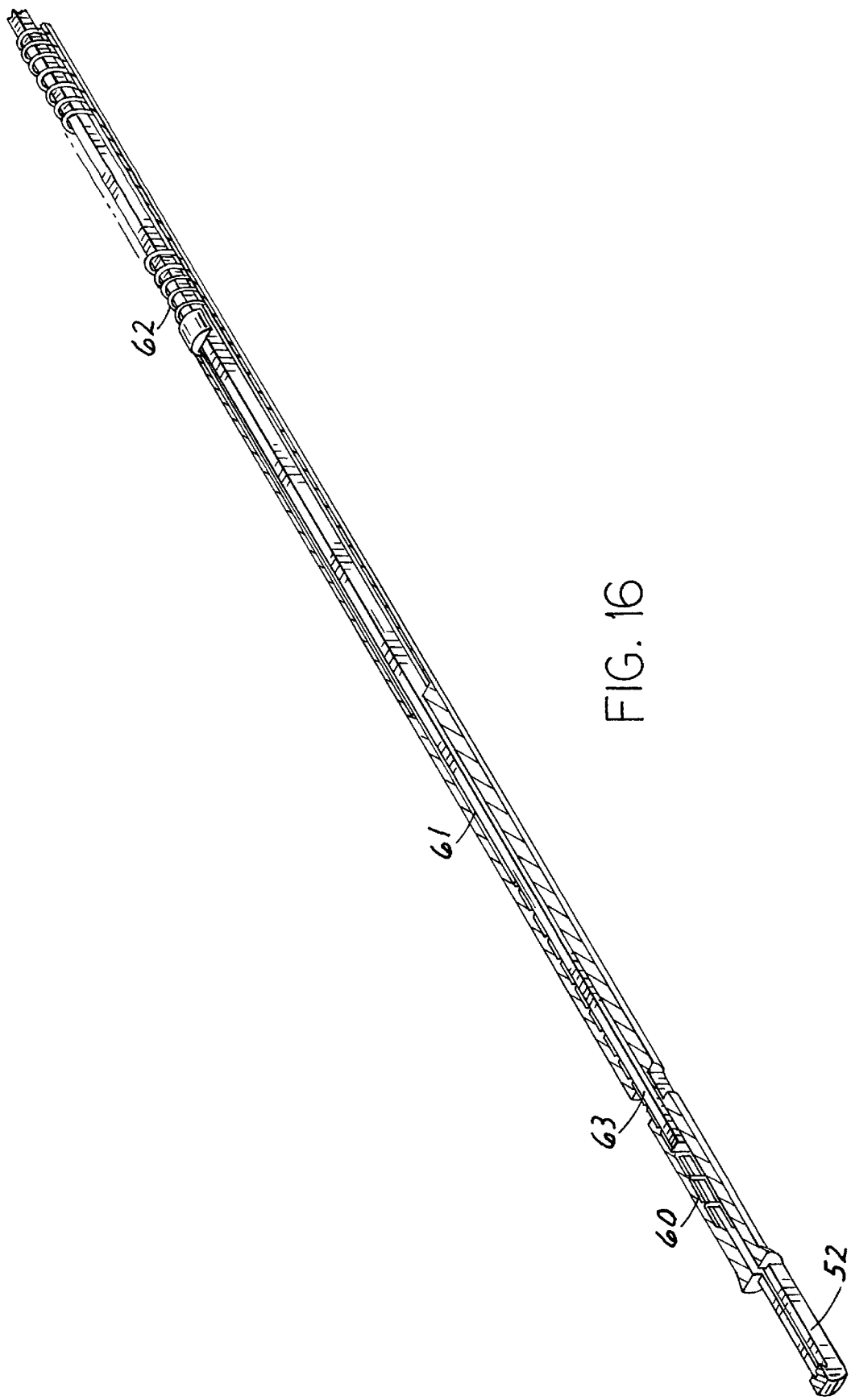
FIG. 16 is a perspective cross sectional view of the clip feeding mechanism for the device of FIG. 12.

In FIG. 16, clips 60 are shown stacked in a head-to-tail configuration. Spring 62 forces stack driver 61 distally, pushing it against the rearward clip in the stack. The proximal end of the spring interacts with the clip forming driver 63 to maintain tension on the clips during clip forming and advancing procedures.

When the instrument is actuated, outer tube 51 and pusher 63 are advanced together. The outer tube slides over and closes the distal ends of jaws 52 & 53. With the outer tube stopped in its full forward position, the pusher continues advancing to its full forward position. On the pusher's return stroke, it re-engages with the outer tube 51 and returns it to its starting position. To ensure this sequential movement, the instrument incorporates a movement separation mechanism. Fundamental to this mechanism is the retaining spring 64 which is connected to the proximal end of outer tube 51. The spring has leaflet-like elements 205 with protrusions 206 on the ends. The protrusions fit into the groove 208 of connector 66. This groove has a tapered surface 207 permitting the protrusions to disengage from the connector during the forward stroke. This connector-spring coupling mechanism is located within a cut-out 209 in the handle 54. When the trigger 54 is pulled, actuating the device, crank 59 advances connector 66 and clip forming driver 63 attached to connector 66 with locking pin 69. The angular surface 207 of the groove in connector 66 will press against the protrusions 206 at the end of the retaining spring leaflets. The protrusions 206 of the retaining spring leaflets are forced by connector 66 to move the retaining spring 64 and outer tube 51 toward the distal end of the device. Once retaining spring 64 reaches the distal end of the cavity 209 of the handle, movement of the outer tube is stopped, thus completing jaw closure. Tapered surface 207 flares the leaflet-like elements 205 allowing connector 66 and clip forming driver 63 to advance and perform the clip forming procedure. Retaining spring 64 and outer tube 51 remain in their full forward position, keeping jaws 52 & 53 closed. When the trigger 56 is released, spring 65 returns the device to its pre-activation configuration. As connector 66 returns, the locking pin 69 pulls back pusher 63. Midway in the return stroke, the spring leaflet protrusions 206 return to the grooves in connector 66, and the jaw closure outer tube retracts allowing the jaws to open.

While the foregoing is a complete and detailed description of preferred embodiments of the disclosed device, numerous variations and modifications may also be employed to implement the purpose of the invention. And, therefore, the elaboration provided should not be assumed to limit the scope of the invention which is intended to be defined by the appended claims.

What we claim is:

1. A ligating clip applier that permits the isolation and inspection of the tissue to be ligated and produces a ligature that inflicts minimal tissue damage which comprises:

a handle assembly, including an activating mechanism, an elongated shaft, containing a clip driver, connected to said activating mechanism and extending distally from said handle, and a pair of jaws connected to the distal end of said elongated shaft said jaws including means, at the distal end of each jaw, for interlocking with each other and being responsive to sequential activation to close then to interlock, forming an enclosure for the isolation of tissue to be ligated, and coordinated tracks on said jaws for guiding a clip advanced by said driver into the distal end of said interlocked jaws where the distal ends of said clip are converged and pass unopposed to encircle and ligate tissue.

2. A ligating clip applier according to claim 1 further comprising a clip size adjustment means to control the distance between the distal end of the locked jaws and the distal end of the clip driver.

3. A ligating clip applier according to claim 1 wherein the jaws are closed by distal movement of an outer tube of the elongated shaft.

4. A ligating clip applier according to claim 1 wherein the shaft contains a supply of clips.

5. A ligating clip applier according to claim 1 wherein the clip driver includes means for advancing the clip into the interlocked jaws.

6. A ligating clip applier according to claim 1 wherein one of said pair of jaws has a double track so as to accommodate the unopposed, converging clip leg.

7. A method of applying a ligating clip to tissue structure said method comprising:

enclosing the tissue within a pair of jaws attached to the distal end of a ligating instrument, interlocking said jaws at a distal point on each jaw, forming the clip around the tissue structure by advancing the clip through guiding tracks within the inner surface of said jaws, and converging and passing, unopposed, the distal ends of said clip around the tissue structure by continuing to advance the clip into the inner distal surface of said interlocked jaws.

8. A ligating clip applier according to claim 1 wherein the activating mechanism further comprises a clip-size adjustment means which simultaneously transforms a single trigger motion into a jaw interlocking action, a clip advancing action and a clip forming action, said clip forming action being adjustable, controlling the distance between the distal end of the interlocked jaws and the distal end of the clip driver in its full forward position.

* * * * *